United States Patent [19]

Notermann

[11] Patent Number: 4,994,589
[45] Date of Patent: Feb. 19, 1991

[54] CATALYTIC SYSTEM FOR EPOXIDATION OF ALKENES

[75] Inventor: Thomas M. Notermann, Charleston, W. Va.

[73] Assignee: Union Carbide Chemicals and Plastics Company Inc., Danbury, Conn.

[21] Appl. No.: 401,541

[22] Filed: Aug. 31, 1989

Related U.S. Application Data

[63] Continuation of Ser. No. 765,066, Aug. 13, 1985, abandoned.

[51] Int. Cl.$^5$ .......................................... C07D 301/10
[52] U.S. Cl. ................................................... 549/534
[58] Field of Search ........................................ 549/534

[56] References Cited

U.S. PATENT DOCUMENTS 3,990,507  4/1976  Boreskov et al. .................. 423/626
4,379,134  4/1983  Weber et al. ....................... 423/626

FOREIGN PATENT DOCUMENTS 3642     8/1979   European Pat. Off. .
431112  12/1975   U.S.S.R. .
590479   7/1947   United Kingdom .
2933950  3/1981   United Kingdom .

Primary Examiner—Richard L. Raymond
Assistant Examiner—Raymond Covington
Attorney, Agent, or Firm—Sharon H. Hegedus

[57] ABSTRACT

A process is provided for epoxidation of an alkene in the presence of an oxygen-containing gas which comprises contacting the alkene and the oxygen-containing gas under epoxidation conditions in the presence of at least one gaseous efficiency-enhancing member of a redox-half reaction pair and a supported silver catalyst, the catalyst comprising a catalytically effective amount of silver on a solid porous support having a stability-enhancing morphology and an efficiency-enhancing amount of at least one efficiency-enhancing salt of a member of a redox-half reaction pair, the support having a surface area of at least about 0.7 $m^2/g$ and a particulate matrix which contains particles having at least one substantially flat major surface.

10 Claims, 1 Drawing Sheet

CATALYTIC SYSTEM FOR EPOXIDATION OF ALKENES

This application is a continuation of prior U.S. application Ser. No. 765,066, filed Aug. 13, 1985, now abandoned.

TECHNICAL FIELD

The present invention is directed to an improved system for the preparation of alkene oxide from alkene and an oxygen-containing gas employing a supported silver catalyst and to the catalysts used in the system. More particularly, the present invention relates to the oxidation of alkenes to the corresponding epoxides in which enhanced performance is attained by combination of a gaseous member of a redox-half reaction pair present in the gaseous mixture of oxygen and alkene, a salt of a member of a redox-half reaction pair in combination with the catalyst and use of a support having a stability-enhancing morphology.

BACKGROUND ART

The production of alkene oxides, or epoxides, particularly ethylene oxide by the direct oxidation of the corresponding alkene in the presence of a silver-containing catalyst has been known for many years. For example, the basic process was described by Defort in U.S. Pat. No. 1,998,878 and by Van Peski in U.S. Pat. No. 2,040,782. The basic reaction proceeds, as illustrated for ethylene, according to the equation:

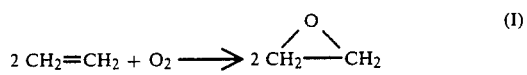
(I)

and production of an unwanted by-product according to the reaction:

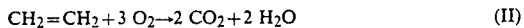
(II)

or by further oxidation of the epoxide.

In the years between the Van Peski patent and the present inventions, research efforts have been directed to improving both the activity and longevity or useful life of the catalyst and the efficiency of the overall catalytic reaction. As is indicated by reactions I and II, the oxidation of an alkene may produce either the alkene oxide (I) sought in the process or the by-products $CO_2$ and $H_2O$.

Several terms are commonly used to describe some of the parameters of the catalytic system. For instance, "conversion" has been defined as the percentage of alkene fed to the reactor which undergoes reaction. The "efficiency" or, as it is sometimes called, the "selectivity" of the overall process is an indication of the proportion, usually represented by a percentage, of the converted material or product which is alkene oxide. The commercial success of a reaction system depends in large measure on the efficiency of the system. At present, maximum efficiencies in commercial production of ethylene oxide by epoxidation are in the low 80s, e.g., 80 or 81 percent. Even a very small increase in efficiency will provide substantial cost benefits in large-scale operation. For example, taking 100,000 metric tons as a typical yearly yield for a conventional ethylene oxide plant and assuming 80 percent conversion, an increase in efficiency of from 80 to 84 percent, all other things being equal, would result in a savings of 3790 metric tons of ethylene per year. In addition, the heat of reaction for reaction II (formation of carbon dioxide) is much greater than that of reaction I (formation of ethylene oxide) so heat-removal problems are more burdensome as the efficiency decreases. Furthermore, as the efficiency decreases, there is the potential for a greater amount of impurities to be present in the reactor effluent which can complicate separation of the desired alkene oxide product. It would be desirable, therefore, to develop a process for the epoxidation of alkene in which the efficiency is greater than that obtained in conventional commercial processes, e.g., with ethylene, efficiencies of 84 percent or greater, while maintaining other performance characteristics, particularly the activity, as described below, in a satisfactory range.

The product of the efficiency and the conversion is equal to the yield, or the percentage of the alkene fed that is converted into the corresponding oxide.

The "activity" of the catalyst is a term used to indicate the amount of alkene oxide contained in the outlet stream of the reactor relative to that in the inlet stream. Activity is generally expressed in terms of pounds of alkene oxide produced per cubic foot of catalyst per hour at specified reaction conditions and rate of feed. The activity may also be stated in terms of the amount of ethylene oxide in the outlet stream or the difference between the ethylene oxide content of the inlet and outlet streams.

If the activity of a reaction system is low, then, all other things being equal, the commercial value of that system will be low. The lower the activity of a reaction system, the less product produced in a unit time for a given feed rate, reactor temperature, catalyst, surface area, etcetera. A low activity can render even a high efficiency process commercially impractical. For production of ethylene oxide, an activity below 4 pounds of ethylene oxide per hour per cubic foot of catalyst is unacceptable for commercial practice. The activity is preferably greater than 8 pounds, and in some instances an activity greater than 11 pounds of alkene oxide per hour per cubic foot of catalyst is desired.

In some instances, activity is measured over a period of time in terms of the amount of alkene oxide produced at a specified constant temperature. Alternatively, activity may be measured as a function of the temperature required to sustain production of a specified constant amount of alkene oxide. Plots of such measurements yield "aging rates" which reflect the stability or useful life of the catalyst. The useful life of a reaction system is the length of time that reactants can be passed through the reaction system during which acceptable activity is observed. The area under a plot of activity versus time is equal to the number of pounds of alkene oxide produced during the useful life of the catalyst per cubic foot of catalyst. The greater the area under such a plot, the more valuable the process is since regeneration or replacement of the catalyst involves a number of expenses, sometimes referred to as turnaround costs. The rate at which activity decreases, i.e., the rate of deactivation at a given point in time, can be represented by the slope of the activity plot, i.e., the derivative of activity with respect to time:

deactivation = d[activity]/dt.

The average rate of deactivation over a period of time can be represented then by the change in activity divided by the time period:

average deactivation = Δactivity/Δt.

At some point, the activity decreases to an unacceptable level, for example, the temperature required to maintain the activity of the system becomes unacceptably high or the rate of production becomes unacceptably low. At this point, the catalyst must either be regenerated or replaced. Some of these definitions may be represented as set out below:

$$\% \text{ Conversion} = \frac{\text{moles alkene reacted}}{\text{moles alkene fed}} \times 100$$

$$\% \text{ Efficiency} = \frac{\text{moles alkene oxide produced}}{\text{moles alkene reacted}} \times 100$$

$$\% \text{ Yield} = \frac{\text{moles alkene oxide produced}}{\text{moles alkene fed}} \times 100$$

Typically, in commercial production, since the outlet or effluent stream emanating from the reactor may contain substantial amounts of unreacted alkene, the effluent stream is recycled and combined with the feedstream after removal of at least a portion of the alkene oxide. Generally, as the activity of a catalyst decreases with time, in order to obtain the same ultimate yield of epoxide product, the effluent stream must either be recycled a greater number of times or the temperature within the reactor must be raised to increase the activity of the catalyst. The former approach to increasing the yield of product requires additional energy expenditures and the latter, which is most frequently used, causes faster catalyst deterioration.

As used herein, an activity-reducing compound refers to a compound which, when present in an activity-reducing amount, causes a reduction in activity, some or all of which activity may subsequently be regained by returning to a situation in which the concentration of the compound is below the minimum activity-reducing amount. The minimum activity-reducing amount varies depending on the particular system, the feedstream and the activity-reducing compound.

Conversely, deactivation, as used herein, refers to a permanent loss of activity, i.e., a decrease in activity which cannot be recovered. As noted above, activity can be increased by raising the temperature, but the need to operate at a higher temperature to maintain a particular activity is representative of deactivation. Furthermore, catalysts tend to deactivate more rapidly when reaction is carried out at higher temperatures.

In contrast to problems associated with low or decreasing catalyst activities, less than satisfactory efficiencies result in loss of starting material, the alkene, as the unwanted product $CO_2$. Ultimately, this also increases product costs.

To be considered satisfactory, a catalyst must not only have a sufficient activity and the catalytic system provide an acceptable efficiency, but the catalyst must also demonstrate a minimum useful life or stability. When a catalyst is spent, typically the reactor must be shut down and partially dismantled to remove the spent catalyst. This results in losses in time and productivity. In addition, the catalyst must be replaced and the silver salvaged or, where possible, regenerated. Even when a catalyst is capable of regeneration in situ, generally production must be halted for some period of time. At best, replacement or regeneration of catalyst requires additional losses in time to treat the spent catalyst and, at worst, requires replacement of the catalyst with the associated costs.

Since even small improvements in activity, efficiency or useful life may have significance in large scale commercial production, such improvements have been the object of a great deal of research in the direct epoxidation of alkenes. The focus of attempts to improve performance, such as the activity and useful life of the catalyst and the efficiency of the system, has included such areas as feedstream additives or removal of components therefrom; methods of preparation of the catalyst; deposition or impregnation of a particular type or form of silver; composition, formation, physical properties and morphology of the support; additives deposited on or impregnated in the support; shape of support aggregates used in the reactor; and various types of reactors and bed designs, such as stationary and fluidized beds.

Early work on the silver-catalyzed direct oxidation of alkenes to alkene oxides in many instances resulted in improvements in activity and particularly the selectively of the system, in many cases the efficiency increasing by several percent. However, recent modifications in such systems have resulted in only small incremental improvements in efficiency. In terms of operating costs, even fractions of a percent improvement in efficiency can translate into large savings in production. Accordingly, current research is still being directed to improvements in the activity and useful life of the catalyst and selectivity of the system.

Although a vast number of elements and compounds are known to have effective catalytic properties in various reactions, many have at least one shortcoming, such as very high cost and/or limited availability, thermal instability in the temperature range in which the reaction is to be conducted, low mechanical strength, small surface area per unit of volume, susceptibility to poisoning, short useful lifetime, etcetera. Such undesirable characteristics make such substances of limited utility as catalysts. Some of these shortcomings, however, may be overcome and in some instances the effectiveness of the catalyst may be improved by applying the substance to a carrier or support.

New support materials are continuously being tried. However, many of those which were employed in the early development of the silver-bearing catalysts are, with some modifications, still being used. Materials which have found most widespread use are typically inorganic and generally are of a mineral nature. Such materials commonly include alumina, fire brick, clay, bauxite, bentonite, kieselguhr, carbon, silicates, silica, silicon carbide, zirconia, diatomaceous earth, and pumice.

In addition to the physical strength of the support materials, other physical properties, such as surface area, pore volume, pore dimensions, and particle size have drawn considerable attention. These properties have been examined with great scrutiny when evidence indicated that there was a correlation between the size of silver particles and the efficiency of the overall system or useful life of the catalyst. Some materials are also preferred for their chemical properties, i.e., their "inertness" or "promoting" properties.

The support serves a number of functions in a heterogeneous catalytic system. Ease of handling is facilitated by a support which generally takes the form of discrete particles or aggregates of varying shape or size which, depending on usage, have a major dimension of about 1 millimeter to about 20 millimeters. Thus it is not necessary for the catalyst to form a permanent or semi-permanent part of the reactor.

The support, however, serves primarily to increase the surface area of the "active" component of the catalyst, silver, which is important in that most epoxidation occurs at the silver surface-fluid interface. Many of the substances commonly employed as catalyst supports not only have the usual external surface, which provides a varying surface area, depending on the shape of the support bodies and the packing of the bodies, but are also of a porous nature and, therefore, have a large internal surface which contributes to the overall surface area of the supported catalyst. Such support materials provide a greater capacity for sorbing not only the catalyst material during catalyst preparation, when the support is impregnated with a solution containing the catalyst component(s) in soluble form, but also a greater capacity for the flow of the fluid reactants within the catalyst during the reaction for which the catalyst is intended. The support also improves performance by lowering the pressure drop through the reactor and by facilitating heat and mass transfer.

Among the large variety of substances employed in the past as supports for catalytic materials, alumina has exhibited superiority in many respects as a catalyst support material. In addition to the low cost of the material, alumina has good thermal stability and some forms have a relatively large surface area.

Alumina, in its various forms, particularly alpha-alumina, has been preferred as a support material for silver-containing catalysts in the preparation of alkene oxides. Numerous variations of surface area, pore dimensions, pore volume and particle size have been suggested as providing the ideal physical property or combination of properties for improving efficiency, activity or useful life of the catalyst.

Holler (U.S. Pat. No. 3,908,002) discloses an alpha-alumina, useful as a catalyst support for reactions conducted at temperatures below 800 degrees C., such as oxidation reactions of hydrocarbons to oxyhydrocarbons. The support, having a surface area reported to be at least about 40 m$^2$/g, is produced by thermally decomposing a porous aluminum ion chainbridged, polymeric carboxylate. Indicating that a large surface area in a carrier may be detrimental to its efficient operation and catalyst activity, Belon (U.S. Pat. No. 3,172,866) describes a method of producing a macroporous catalyst carrier which may be used in the catalytic production of ethylene oxide having pore diameters of between 0.1 and 8.0 microns and a specific surface area between a few square meters and one square decimeter per gram. The support is prepared by heating a mixture of active and calcined aluminum oxides and a small amount of boron oxide at temperatures of between about 1,600 and 1,800 degrees C. Waterman (U.S. Pat. No. 2,901,441) describes a process for preparing highly active and selective catalysts for the oxidation of olefins to olefin oxides on a support having an average porosity of at least 35 percent. The method involves washing an alpha-alumina or silicon carbide support having an average porosity of between 35 and 65 percent with an aqueous solution of lactic acid, washing with water until neutral, and then impregnating the support with an aqueous solution of silver lactate. The impregnated support is thereafter heat-treated to deposit elemental silver. A silver-supported catalyst for the vapor phase oxidation of ethylene to ethylene oxide, exhibiting improved production of ethylene oxide and catalyst longevity, is described by Brown et al (U.S. Pat. No. 3,725,307). The catalyst is disclosed as being formed from support particles having an average pore diameter of at least 10 microns up to, preferably, 70 microns and a surface area of less than about 1 m$^2$/g. The selectivities reported do not range above about 73 percent. The support is preferably composed of silica-alumina. A silver-supported catalyst which includes a support of alpha-alumina, silicon carbide, fused aluminum oxide, or mixtures of alumina and silica was asserted by DeMaio (U.S. Pat. No. 3,664,970) to eliminate the need for halogenated inhibitors in the oxidation of ethylene to ethylene oxide. The support is composed of particles having a minimum apparent porosity of about 30 percent and wherein at least 90 percent of the pores have diameters in the range of 1 to 30 microns, the average of the diameters being in the range of 4 to 10 microns. Wattimena (U.S. Pat. No. 3,563,914) discloses silver catalysts using aluminum oxide supports having pore volumes between 15 and 30 ml/g and surface areas below about 10 m$^2$/g.

Hayden et al (U.K. Patent Application 2,014,133) disclose a silver catalyst employing a support having a specific surface area in the range of 0.05 to 10 m$^2$/g, an apparent porosity of at least 20 percent, and mean pore diameters of 0.1 to 20 microns, the pore size distribution being bimodal, in which the smaller pores preferably account for at least 70 percent of the total pore volume. Alpha-alumina supports are described by Rashkin (U.K. Patent Application 2,122,913A) having a "relatively low surface area" of less than 30 m$^2$/g. Mitsuhata et al (Japanese Published Patent Application 56-089843) and Mitsuhata et al (U.S. Pat. No. 4,368,144) describe supported silver catalysts in which the support is formed from alpha-alumina having a specific surface area of 0.5 to 5 m$^2$/g. Watanabe et al (Japanese Published Patent Application 56-105750) employ a similar catalyst support having a surface area of 1 to 5 m$^2$/g. Hayden et al (U.S. Pat. No. 4,007,135) describe silver-containing catalysts in which the porous heat-resisting support has a specific surface area in the range of 0.04 to 10 m$^2$/g, an apparent porosity of at least 20 percent, and a median pore diameter of 0.3 to 15 microns. Mitsuhata et al (U.S. Pat. No. 4,248,740) describe the use of high alpha-alumina content supports having a specific surface area of not more than 10 m$^2$/g, an apparent porosity of 40 to 60 percent by volume, and a pore volume of 0.1 to 0.5 cc/g. Armstrong et al (U.S. Pat. No. 4,342,667) disclose a supported silver catalyst, useful in the oxidation of ethylene to ethylene oxide, in which the support has a surface area of 0.02 to 2 m$^2$/g, an average pore diameter of 0.5 to 50 microns and an average pore volume of 0.2 to 0.5 cc/g.

There has also been some interest in the purity of supports employed, both as to composition and phase. Examples of high purity alumina include U.S. Pat. No. 2,901,441 which uses alpha-alumina having a purity of about 99.5 percent as a support for catalysts used to oxidize olefins to olefin oxides. An ethylene oxidation catalyst is disclosed in German Patent Publication DE 2,933,950 which attains a long catalyst life without a loss in activity or selectivity by using an alpha-alumina support having less than 0.001 weight percent of alkali-soluble silicon compounds. The catalyst is prepared by boiling commercial quality alpha-alumina with 1 weight percent sodium hydroxide solution and washing to a pH value of 8. If desired, the silicon compound concentration may be reduced below 1 part per million (ppm) by washing further with 1 weight percent HF. U.K. Patent Application 2,122,913A describes supported silver catalysts in which the support is composed of silica, alumina or mixtures thereof, one example of which is an alumina having a purity of 99.3 percent by weight. The silver-supported catalyst described in Japanese Published Patent Application 56-089843 employs an alpha-alumina carrier having a sodium content of less than 0.07 weight percent. Japanese Published Patent Application 56-105750 describes the use of an alpha-alumina support in conjunction with a silver catalyst for producing ethylene oxide, which support has a sodium content less than 0.07 weight percent. A silver catalyst including an alpha-alumina carrier having a sodium content of not more than 0.07 percent is described by Mitsuhata et al (U.S. Pat. No. 4,368,144). The support also has a surface area within the range of 0.5 to 5 $m^2/g$, an apparent porosity of 25 to 60 percent, a specific pore volume of 0.2 to 0.5 cc/g, and a particle diameter within the range of 3 to 20 mm. An alpha-alumina support having a purity of 98+ weight percent, for use with silver in the catalytic oxidation of ethylene, is described by Warner et al in U.S. Pat. No. 4,455,392. The patent additionally discloses that the carrier is generally a conventional microporous support with surface areas of less than 10 $m^2/g$, pore volumes ranging from about 0.15 to 0.8 cc/g, and pore diameters of about 0.1 to 100 microns.

In addition to compositional purity, both phase purity and morphology of the support have been areas in which improvements in efficiency, selectivity or stability of the catalyst have been sought. Examples include U.S. Pat. No. 2,901,441 in which aluminum oxide is substantially completely converted to the alpha form of alumina by heating aluminum oxide to a temperature of about 1,500 to 2,050 degrees C. Weiss (U.S. Pat. No. 2,209,908) and Carter (U.S. Patent 2,294,383) describe the use of "Tabular Corundum" as a catalyst support for metallic oxides, such as those oxides of metals selected from the fifth and sixth group of the periodic system, for example, vanadium, molybdenum, uranium, etcetera, in the oxidation of various organic materials to maleic acid and maleic anhydride and silver for the catalytic oxidation of ethylene to ethylene oxide, respectively. Weiss indicates that Tabular Corundum, which is almost entirely aluminum oxide and has the alpha-corundum crystalline form of aluminum oxide, may be formed by mixing aluminum oxide with one or more of several compounds, such as sodium oxide and chromic oxide, and heating the mixture to a temperature in the range of about 800 to about 1,800 degrees C. Tabular Corundum is further described as having impurities present in only small quantities, the material also includes "readily bonded surfaces and consisting essentially of interlocked corundum crystals in tabular form, having the contained impurities disseminated in minute globules throughout the crystalline alumina". Brengle et al (U.S. Pat. No. 2,709,173) also employ Tabular Corundum as a support in one of their examples.

U.S. Pat. Nos. 4,039,481 and 4,136,063 to Kimura et al disclose a catalyst carrier and a method for making same, the catalyst being the type used in catalytic converters in automobile exhaust systems. Specifically, the catalysts have a surface layer containing alpha-phase alumina and an inner portion consisting essentially of alumina of a phase other than that of the alpha phase. The pores in the alpha-alumina surface layer are larger than those in the inner portion of the catalyst body. A method of preparing the phase gradient support particles is described which provides for treating the surface of the alumina to a depth of about 400 microns with a transition element, particularly iron, and thereafter firing the carrier particles.

Weber et al (U.S. Pat. No. 4,379,134) describe high purity alpha-alumina bodies, at least 85 percent of the pore volume of the bodies having pores with a diameter of from 10,000 to 200,000 Angstroms. The high purity alpha-alumina bodies are prepared by peptizing boehmite in an acidic aqueous, fluoride anion-containing mixture. An extrudable mixture is formed thereby which is extruded and shaped into formed bodies which are thereafter dried at 100 to 300 degrees C., calcined at a temperature of from 400 to 700 degrees C. to convert the alumina to the gamma phase, and subsequently calcined further at a temperature of from 1,200 to 1,700 degrees C. to convert the gamma phase to alpha-alumina phase.

A method of producing granulated porous corundum having a homogeneous porous structure with a total pore volume of 0.3 to 1.0 $cm^3/g$ and a predominant pore size of 5,000 to 30,000 A is described by Boreskov et al (U.S. Pat. No. 3,950,507). The method of preparing the alpha-alumina includes treating active alumina or aluminum hydroxide having a porous structure to a first heat treatment in which the temperature is increased from 20 to 700 degrees C., a second heat treatment in the range of from 700 to 1,000 degrees C., and a third treatment in the range of from 1,000 to 1,400 degrees C. Each of the heat treatments is for a period of at least one-half hour, the first heat treatment being conducted in an atmosphere of hydrogen fluoride in which the alumina absorbs the hydrogen fluoride and the second heat treatment desorbs the hydrogen fluoride. The patent also describes a similar procedure employing stationary thermal conditions in which the granules of alumina or aluminum hydroxide are impregnated with other fluorine-containing substances prior to the first thermal treatment. The recommended starting materials used to form alpha-alumina include granulated pseudo-boehmite, boehmite or bayerite as the granulated aluminum hydroxide and granulated alpha-, eta-, or theta-alumina as the active alumina.

Although alpha-alumina has been considered by most to be the preferred alumina support material, Smith et al (U.S. Pat. No. 2,422,172) have suggested that beta-aluminas are more desirable than the alpha phase as a support material for catalysts, particularly those used in catalytic conversion processes such as dehydrogenation and hydroforming.

In seeking the ideal support material, there has been some departure from the commonly employed substances. For example, some use has been made of alkali metal and alkaline earth metal carbonates, both as the sole support material and in combination with other materials as the carrier for processes such as direct oxidation of alkenes to epoxides.

A number of supported silver-containing catalysts have been employed for epoxidation of alkenes in which the carrier includes, sometimes labelled as a promoter, a carbonate of a metal, generally an alkali metal or alkaline earth metal. Some examples of the use of one or more alkali and/or alkaline earth carbonates may be found in U.S. Pat. Nos. 2,424,084, 2,424,086, 2,615,900, 2,713,586, 3,121,099, 3,258,433, 3,563,913, 3,563,914, 3,585,217, 4,007,135, 4,033,903, 4,039,561, 4,066,575, 4,094,889, 4,123,385, 4,125,480, 4,168,247, 4,186,106, 4,226,782, 4,229,321, 4,324,699, European Patent Publications 0,003,642 and 0,011,356, Japanese Patents 41-11847 and 57-107242, U.K. Patents 590,479, 1,571,123 and 2,014,133A, and Murray, "A Study Of The Oxidation Of Ethylene To Ethylene Oxide On A Silver Catalyst", *Australian Journal of Scientific Research*, Volume 3A, Pages 433–449 (1950). In addition, U.S. Pat. No. 3,332,887 employs zinc and/or cadmium carbonates, Gelbstein, (DS 2,352,608) discloses the use of the latter carbonate and European Patent Publication 0,003,642 mentions the use of molybdenum carbonate.

Several patents have described the use of fluorine-containing substances to treat support materials, in some cases to provide a compositionally pure support, and in other cases as a fluxing agent to improve the phase purity of the support. Thus, U.K. Published Patent Specification 590,479 and U.S. Pat. No. 2,424,086 indicate that a more active catalyst is formed if the support material has undergone a preliminary treatment with a dilute solution of hydrofluoric acid prior to impregnation with silver. U.S. Pat. No. 4,379,134 teaches the preparation of high purity alpha-alumina bodies by peptizing boehmite alumina in an aqueous acidic mixture containing fluoride anions and water. German Patent 2,933,950 teaches the reduction of silicon content by treatment with HF. U.S. Pat. No. 3,950,507 teaches the preparation of granulated porous corundum by a multiple step heat treatment in which initial steps may be carried out in an atmosphere of hydrogen fluoride. Hosoda et al (U.S. Pat. No. 3,144,416) suggest that a small amount of a halogen compound, sulfur compound, nitrogen compound, or phosphorous compound may be added either to the reaction gas or the catalyst to improve the selectivity of the catalyst.

The nature of the silver itself has also been examined and modified in attempts to improve the efficiency and stability of the catalyst. Cavitt (U.S. Pat. No. 4,229,321) teaches that a supported silver catalyst of improved selectivity and activity may be prepared by mechanically removing the outer surface or skin of the catalyst after the impregnated catalyst has been heated to evaporate volatile material and reduction of the silver salt to silver metal, thereby activating the catalyst.

Since the early work on the direct catalytic oxidation of ethylene to ethylene oxide, workers in the field have suggested that the addition of certain compounds to the gaseous feedstream or direct incorporation of metals or compounds in the catalyst could enhance or promote the production of ethylene oxide. Such metals or compounds have been known variously as "anti-catalysts", "promoters" and "inhibitors". These substances, which are not themselves considered catalysts, have been proposed by prior workers to contribute to the efficiency of the process by inhibiting the formation of carbon dioxide or promoting the production of ethylene oxide. The scientific literature is replete with examples of the use of alkali metals and alkaline earth metals and their cations to promote the efficiency of silver catalysts used in epoxidation reactions. For example, sodium, potassium and calcium were disclosed as being suitable promoters in U.S. Pat. No. 2,177,361. Numerous examples may be found in literature of preference for one or several metals or cations and exclusion of one or more metals or cations as promoters in silver catalysts.

Among those anions associated with the cation promoters used in preparing silver-containing catalysts employed in direct epoxidation reactions that have been suggested as being suitable include carboxylates, for example, formate, acetate, malonate, oxalate, lactate, tartrate, and/or citrate, and inorganic salts, such as carbonates, bicarbonates, phosphates, nitrates, and/or nitrites, chlorides, iodides, bromates, and isopropoxides. However, although many examples may be found in the literature indicating that such compounds are suitable, numerous patents, such as U.S. Pat. Nos. 3,962,136; 4,012,425; 4,066,575; 4,207,210; and 4,471,071, suggest that no unusual effectiveness, particularly with regard to catalytic activity, is observed with any particular anion of an alkali metal promoter. U.S. Pat. Nos. 4,007,135; 4,094,889; 4,125,480; 4,226,782; 4,235,757; 4,324,699; 4,342,667; 4,356,312; 4,368,144; and 4,455,392 disclose that potassium nitrate may be added to the catalyst as a suitable promoting material. Potassium nitrate may also be formed in situ when a carrier material is treated with certain amines in the presence of potassium ions as, for instance, when silver is introduced to a carrier material in a silver-impregnating solution containing an amine and potassium ions, followed by roasting.

A number of compounds have been proposed in the literature as additives to the feedstream or reactants to improve the efficiency of the direct, silver-catalyzed oxidation of alkenes to alkene oxides. For example, Law and Chitwood (U.S. Pat. No. 2,194,602) disclose the use of a "repressant", i.e., anti-catalyst, such as ethylene dichloride, chlorine, sulfur chloride, sulfur trioxide, nitrogen dioxide, or other halogen-containing or acid-forming materials. Numerous additional anti-catalysts are presented by the same patentees in U.S. Pat. No. 2,279,469. The anti-catalysts, broadly listed in categories such as halogens and compounds containing halogen, hydrocarbons, compounds containing carbon, hydrogen and oxygen, compounds containing sulfur, and compounds containing nitrogen are represented and, in addition to those compounds already mentioned above, additional representative compounds include, as nitrogen-containing compounds, nitric oxide, ammonia, amines such as ethylenediamine, diphenylamine and analine, nitro compounds such as o-nitroanisole and o-nitrotoluene as organic oxygen-containing organic compounds, alcohols such as methyl, ethyl and isopropyl alcohols, ethers such as isopropyl and dibutyl ethers, as well as glycol ethers, ketones such as methyl ethyl ketone and acetone, as hydrocarbons such as benzene, and N-hexane; sulfur compounds such as sulfur dioxide, hydrogen sulfide and diethylsulfide; chlorine-containing compounds such as carbon tetrachloride, chlorobenzene and dichloroethyl ether. Berl (U.S. Pat. No. 2,270,780) lists a number of compounds as anti-detonating or anti-knock materials to control the oxidation of ethylene and propylene to their oxides. Disclosures of other feedstream additives used in the production of alkene oxides, particularly halogen compounds, may be found in U.S. Pat. Nos. 2,279,470; 2,799,687; 3,144,416; 4,007,135; 4,206,128; and 4,368,144. In addition, EPO Patent 0,003,642 and U.K. Patent Application 2,014,133A disclose processes for the production of olefin oxides employing silver-containing catalysts in which a chlorine-containing reaction modifier and a nitrite or nitrite-forming substance are described. Rumanian Patent 53012, published Dec. 2, 1971, discloses a direct, silver-catalyzed direct epoxidation procedure which employs oxides of nitrogen in the feedstream. U.K. Patent 524,007 includes ethylene dichloride or nitrogen dioxide in the feedstream of a silver-catalyzed epoxidation procedure.

Although much of the art discussed above has resulted in improvements in the efficiency, activity or stability of the catalytic system, many of the improvements have individually been rather slight. In some of the catalytic systems, gains in one of these performance parameters have been frequently offset by losses in another; that is, enhancement of one index of performance has been accompanied by a deleterious effect on another of the indices. For example, if a reaction system is designed which has a very short useful life, the system may be commercially impractical even though the efficiency and initial activity of the catalyst are outstanding. Accordingly, a system that provides an increase in the efficiency of the overall catalytic reaction system, while only minimally decreasing the activity and useful life of the catalyst would be particularly beneficial.

DISCLOSURE OF THE INVENTION

The present invention is directed to a catalytic process for epoxidation of alkene in the presence of an oxygen-containing gas and to the catalyst used therefor. The process comprises contacting an alkene with an oxygen-containing gas under epoxidation conditions in the presence of at least one gaseous efficiency-enhancing member of a redox-half reaction pair of a redox-half reaction pair and a solid catalyst. The catalyst comprises a catalytically effective amount of silver on a solid support and an efficiency-enhancing amount of at least one efficiency-enhancing salt of a member of a redox-half reaction pair. The support employed for the catalyst has a surface area of at least about $0.7 \text{ m}^2/\text{g}$ and is formed from particles, many of which are interfused or interpenetrating, that is, particles which project from opposing sides of other particles as if passing through or "growing" out of other particles. In addition, such particles have at least one substantially flat major surface.

The present invention is also directed to a catalyst for use in epoxidation of alkene with an oxygen-containing gas which comprises a catalytically effective amount of silver on a solid support and at least one efficiency-enhancing salt of a member of a redox-half reaction pair. The efficiency-enhancing salt is present in an amount which provides an efficiency of at least about 84 percent under Standard Test Conditions. The support has a surface area of at least about $0.7 \text{ m}^2/\text{g}$ and is formed from interfused particles having at least one substantially flat major surface. The combination of a support having a surface area of at least about $0.7 \text{ m}^2/\text{g}$ in which particles have at least one substantially flat major surface and the presence of a salt of a member of a redox-half reaction pair produces a catalyst of enhanced performance which is both highly active and capable of maintaining such activity for extended periods of time. In addition to those indices of performance, a catalytic system employing such a catalyst, particularly when used in the presence of a gaseous member of a redox-half reaction pair, also results in enhancement of efficiency. Thus, efficiencies on the order of about 84 percent are the norm under Standard Test Conditions and of about 88–92 percent or greater are not uncommon. In addition, the catalysts of the present invention are capable of maintaining a high activity or short term stability as well as a long term stability.

BRIEF DESCRIPTION OF THE DRAWING

The figure is a scanning electron micrograph, taken at a magnification of 2000 X, of alpha-alumina support particles having a platelet morphology according to the present invention.

DETAILED DESCRIPTION OF THE INVENTION

The present invention is directed to a process for the vapor phase oxidation of alkenes to alkene oxides, i.e., an epoxidation process, in the presence of an oxygen-containing gas and to the silver catalysts employed therein.

The process and catalyst of the present invention are useful in the epoxidation of the alkenes ethylene and propylene, the epoxides of which are in great demand for use as intermediates in producing such materials as polymers, surfactants, synthetic fibers and antifreeze. However, the present invention is not limited to these compounds but may be used to oxidize cyclic and acyclic alkenes which are in the gaseous state or have significant vapor pressures under epoxidation conditions. Typically these compounds are characterized as having on the order of 12 carbon atoms or less which are gaseous under epoxidation conditions. In addition to ethylene and propylene, examples of alkenes which may be used in the present invention include such compounds as butene, dodecene, cyclohexene, 4-vinylcyclohexene, styrene and norbornene.

Support

The support material used in the present invention may be selected from suitable solid, porous, refractory material which can withstand roasting temperatures, if that is the method employed to reduce the silver present to its free metallic state. Regardless of the method used to reduce the silver, the support should also be able to withstand the temperatures employed within the reactor under epoxidation process conditions. Preferably, the support should not have any undue deleterious effect on the performance of the system. Examples of suitable materials include magnesia, zirconia, silica, silicon carbide, and alumina, preferably alpha-alumina. Suitable support materials also have a surface area of at least about $0.7 \text{ m}^2/\text{g}$ and preferably about 0.7 to about $16 \text{ m}^2/\text{g}$, particularly preferred are those materials having surface areas in the range of about 0.7 to about $7 \text{ m}^2/\text{g}$. The surface area is measured by the conventional B. E. T. method using nitrogen described by Brunauer, Emmet and Teller in *J. Am. Chem. Soc.*, 60, 309–16 (1938).

The support should be composed of a particulate matrix which includes particles having at least one substantially flat major surface. Preferably, at least about 50 percent of particles of the support having a particle size of at least 0.1 micron comprise particles having at least one substantially flat major surface. As used herein, "particle size" refers to the diameter or major dimension of the particle.

The support particles of the present invention, which are provided with at least one substantially flat major surface, may be characterized as having a lamellate or platelet-type morphology wherein some of the particles have two, or sometimes more, flat surfaces. The "substantially flat major surface" referred to herein may be characterized by a radius of curvature of at least about twice the length of the major dimension of the surface. Preferably, the particles also have aspect ratios of at least about 4:1, the aspect ratio being the ratio of the longest or major dimension to the smallest or minor dimension. The particles preferably have aspect ratios exceeding about 10:1. In some aspects of the present invention, the major dimension of a major portion of the particles having platelet-type morphology is less than about 50 microns, preferably less than about 20 microns. When alpha-alumina is employed as the support material, the platelet-type particles frequently have a morphology which approximates the shape of small plates or wafers. The configuration of these plates is shown in FIG. 1. A portion of the support particles preferably are formed as "interfused" or "interpenetrated" platelets, that is, having the appearance of platelets growing out of or passing through one another at various angles. This is particularly true of the preferred material, alpha-alumina. In some cases the edges of some of the platelet or wafer-like particles contact or are fused to the faces of other particles to provide a structure which appears to be an irregular "house of cards" structure. It is this morphology or structure which is believed to account for the crush strength, pore volumes and surface areas which provide the high performance characteristics of the present invention such as the short term stability or high activity and long term stability.

These platelet-type particles frequently have substantially angular edge portions, as contrasted with amorphous or rounded edge portions of conventional support materials, including conventional alpha-alumina supports. The higher surface energies associated with the former type of edge portions may contribute to the enhanced performance of the subject invention.

The carrier materials of the present invention may generally be described as porous or microporous, having median pore diameters of about 0.01 to about 100 microns, preferably about 0.5 to about 50 microns, and most preferably about 1 to about 5 microns. Generally, they have pore volumes of about 0.6 to about 1.4 cc/g, preferably about 0.8 to about 1.2 cc/g. Pore volumes may be measured by any conventional technique, such as conventional mercury porosity or water absorption technique.

Generally improved results have been demonstrated when the support material is compositionally pure and also phase pure. By "compositionally pure" is meant a material which is substantially a single substance, such as alumina, with only trace impurities being present. "Phase purity" or like terms refer to the homogeneity of the support with respect to its phase. In the present invention, alumina, having a high or exclusive alpha-phase purity (i.e., alpha-alumina), is preferred. Most preferred is a material composed of at least 98 percent, by weight, of alpha-alumina. Under some conditions as when used in conjunction with the salt and gaseous members of redox-half reaction pairs, the presence of even small amounts of sodium can adversely affect the activity and useful life of the catalyst, i.e., have a deactivating effect on the catalyst. Improved results have been observed when the support contains leachable sodium levels less than about 50 parts per million (ppm) by weight, preferably less than 40 ppm, and most preferably less than about 20 ppm based on the weight of the total support. Supports which are also useful in the present invention are those having less than a catalyst-deactivating amount of total sodium. This corresponds, in some instances, to a concentration of total sodium of about 200 ppm. Suitable alpha-aluminas having concentrations of leachable sodium below 50 ppm may be obtained commercially from suppliers, such as the Norton Company. Alternatively, suitable alpha-alumina support materials may be prepared so as to obtain leachable sodium concentrations below 50 ppm by the method described by Weber et al in U.S. Pat. No. 4,379,134. In brief, a suitable procedure involves treatment of a support material, particularly alpha-alumina, with an organic or inorganic fluorine-containing material in any solvent capable of dissolving the fluorine-containing substance, preferably in aqueous solution, and thereafter firing the treated support material at a suitable temperature. In the present invention, the support material may either be extruded and formed into pellets after fluorine treatment and before firing or formed, i.e., extruded, pellets may be fluorine-treated and then fired.

Most of the materials found suitable as carriers having flat surfaces may be formed by treating material having another morphology or material lacking the desired flat surface with a suitable agent which serves to recrystallize the material to the desired form. When alpha-alumina is the support to be employed in the catalyst, conversion may be effected by treating other forms of alumina, such as boehmite, aluminum hydroxide, pseudo boehmite, or beta-alumina, preferably gamma or impure alpha-alumina or mixtures of alpha and another alumina, such as mixed alpha/theta-alumina, with an organic or inorganic fluorine-containing substance capable of catalyzing the conversion or transition, i.e., recrystallizing, of the other alumina or impure alumina to alpha-alumina. Suitable fluorine-containing substances include organic or inorganic substances and may be ionic, covalent or polar covalent compounds as well as $F_2$. The fluorine-containing substance should, preferably, be a somewhat volatile material or one which can be readily volatilized under process conditions. Examples of such fluorine-containing substances which can be employed as recrystallizing agents include aluminum fluoride, ammonium fluoride, hydrofluoric acid, and dichlorodifluoromethane.

The fluorine recrystallizing agent is used in an amount sufficient to effect conversion of the alumina to alpha-alumina having at least one substantially flat surface. This will vary with such factors as the process conditions under which the conversion is effected, such as the firing temperature and heating rate, as well as the bed depth of the material to be transformed, the amount of alumina being treated, the level of contamination of the alumina, and how well the firing chamber is sealed. Typically, a suitable amount of fluorine recrystallizing agent is not more than about 3 percent, by weight, based on the weight of support material being treated. Preferably, the recrystallizing agent is present in an amount of about 0.8 to about 2 percent, by weight.

To effect conversions to alpha-alumina, the fluorine-treated alumina is fired at a temperature of less than about 1,200 degrees C., preferably from a temperature of about 750 to about 1,000 degrees C. The properties of the alpha-alumina depend not only on the firing temperature but also, in part, on the rate of heating. With lower levels of fluorine, plate-like crystals having high strength and surface area can be obtained with rapid heating. As used herein, "rapid heating" refers to heating from room temperature to the desired temperature in about 1 recrystallizing agent, slower heating rates are generally preferred to achieve the same type of product. The "slow heating" treatments generally consist of heating from room temperature to about 700 degrees C. in about 0.5 to 1 hour and from about 700 degrees C. to the final temperature at a rate of about 100 degrees C. per hour.

Treatment of an alumina to convert it to alpha-alumina produces not only an alpha-alumina having a flat, platelet-like morphology, but also an alpha-alumina having a relatively large surface area and increased crush strength.

The support particles are preferably formed into aggregates or "pills" of a size and configuration to be usable in commercially operated ethylene dioxide tubular reactors. These pills may be formed by conventional extrusion and firing, as discussed above. When alpha-alumina is the support material, treatment with the fluorine-recrystallizing agent may be performed before or after extrusion. The pills generally range in size from about 2 mm to about 15 mm, preferably about 3 mm to about 12 mm. The size is chosen to be consistent with the type of reactor employed. In general, in fixed bed reactor applications, sizes ranging from about 3 mm to about 10 mm have been found to be most suitable in the typical tubular reactors used in commerce. The shapes of the carrier aggregates useful for purposes of the present invention can vary widely. Common shapes include spheres and cylinders, especially hollow cylinders. Other shapes include amphora (such as defined in U.S. Pat. Nos. 3,848,033, 3,966,639 and 4,170,569), amorphous, Raschig rings, saddles, cross-partitioned hollow cylinders (e.g., having at least one partition extending between walls), cylinders having gas channels from side wall to side wall, cylinders having two or more gas channels, and ribbed or finned structures. While the cylinders are often circular, other cross-sections, such as oval, hexagonal, quadrilateral, trilateral, etcetera, may be useful.

Catalysts

The catalysts of the present invention are conventional to the extent that silver is coated or deposited on and/or within a solid porous carrier. Any known method of introducing the silver to the catalyst support may be employed. Numerous examples and procedures are given in the patents discussed above. In brief, in a coating or suspension process a slurry, preferably aqueous, of the active catlytic material, such as silver or its oxide, is applied to the support to form a coherent silver layer on the support. In the preferred impregnation process, a solution of a soluble salt or complex of silver in an amount sufficient to deposit the desired weight of silver upon the carrier is dissolved in a suitable solvent or "complexing/solubilizing" agent. This solution may be used to impregnate a porous catalyst support or carrier by immersing the carrier in the silver-containing impregnating solution. The impregnating solution is preferably introduced to the catalyst support in a container which has been previously evacuated. Alternatively, the support may be sprayed or sprinkled with the impregnating solution. The excess solution may then be allowed to drain off or the solvent may be removed by evaporation under reduced pressure at a suitable temperature. The silver salt or compound used to form the silver-containing impregnating solution in a solvent or a complexing/solubilizing agent is not particularly critical and any silver salt or compound generally known to the art which is both soluble in and does not react with the solvent or complexing/solubilizing agent to form an unwanted product may be employed. Thus, the silver may be introduced to the solvent or complexing/solubilizing agent as an oxide or a salt, such as nitrate or carboxylate, for example, an acetate, propionate, butyrate, oxalate, malonate, malate, maleate, lactate, citrate, phthalate, generally the silver salts of higher fatty acids, and the like.

The chemical practitioner may choose from a large number of suitable solvents or complexing/solubilizing agents to form the silver-containing impregnating solution. Besides adequately dissolving the silver or converting it to a soluble form, a suitable solvent or complexing/solubilizing agent should be capable of being readily removed in subsequent steps, either by a washing, volatilizing or oxidation procedure, or the like. The complexing/solubilizing agent, preferably, should also permit solution to provide silver in the finished catalyst to the extent of about 2 to about 60 percent silver or higher, based on the total weight of the catalyst. It is also generally preferred that the solvents or complexing/solubilizing agents be readily miscible with water since aqueous solutions may be conveniently employed. Among the materials found suitable as solvents or complexing/solubilizing agents for the preparation the silver-containing solutions are alcohols, including glycols, such as ethylene glycol (U.S. Pat. Nos. 2,825,701 to Endler et al and 3,563,914 to Wattimena), ammonia (U.S. Pat. No. 2,463,228 to West et al), amines and aqueous mixtures of amines (U.S. Pat. Nos. 2,459,896 to Schwartz, 3,563,914 to Wattimena, 3,702,259 to Nielsen, and 4,097,414 to Cavitt, and carboxylic acids, such as lactic acid (U.S. Pat. Nos. 2,477,435 to Aries and 3,501,417 to DeMaio).

Typically, a silver-containing solution is prepared by dissolving silver in a suitable solvent or complexing/solubilizing agent as, for example, a mixture of water, ethylenediamine, oxalic acid, silver oxide, and monoethanolamine. The solution is then mixed with support particles and drained. Thereafter the particles are suitably dried.

After impregnation, the silver-impregnated carrier particles are treated to convert the silver salt or complex to silver metal and thereby effect deposition of silver on the surface of the support. As used herein, the term "surface", as applied to the support, includes not only the external surfaces of the carrier but also the internal surfaces, that is, the surfaces defining the pores or internal portion of the support particles. This may be done by treating the impregnated particles with a reducing agent, such as oxalic acid or alkanolamine and/or by roasting, at an elevated temperature on the order of about 100 to about 900 degrees C., preferably about 200 to about 650 degrees C. to decompose the silver compound and reduce the silver to its free metallic state. The duration of roasting is generally for a period of about 1 to about 10 minutes, depending on the temperature used, and is commonly effectuated in a hot-air belt roaster.

The concentration of silver in the finished catalyst may vary from about 2 percent to 60 percent, by weight, based on the total weight of the catalyst, more preferably the silver concentration ranges from about 8 percent to about 50 percent, by weight. When a "high silver" content catalyst is preferred, the silver ranges from about 30 to about 60 percent, by weight. The preferred concentration for "low silver" content catalyst ranges from about 2 to about 20 weight percent. When a catalyst having a silver concentration in this preferred range is prepared, the silver is preferably introduced in a series of at least two sequential impregnation and roasting cycles, as discussed in greater detail below. Lower silver concentrations are preferred from a capital expense standpoint. However, the optimum silver concentration for a particular catalyst should also take into consideration increased productivity resulting from performance characteristics, such as catalyst activity, system efficiency and the rate of catalyst aging. In many instances higher concentrations of silver are preferred since they demonstrate levels of enhanced performance, particularly catalyst stability, which compensates for the greater capital expenditure.

Efficiency-Enhancing Compound

A preferred aspect of the present invention includes an efficiency-enhancing amount of at least one efficiency-enhancing salt of a member of a redox-half reaction pair. The term "redox-half reaction" is defined herein to mean half-reactions like those found in equations presented in tables of standard reduction or oxidation potentials, also known as standard or single electrode potentials, of the type found in, for instance, "Handbook of Chemistry", N. A. Lange, Editor, McGraw-Hill Book Company, Inc., pages 1213–1218 (1961) or "CRC Handbook of Chemistry and Physics", 65th Edition, CRC Press, Inc., Boca Raton, Florida, pages D155-162 (1984). The term "redox-half reaction pair" refers to the pairs of atoms, molecules or ions or mixtures thereof which undergo oxidation or reduction in such half-reaction equations. A member of a redox-half reaction pair is, therefore, one of the atoms, molecules or ions that appears in a particular redox-half reaction equation. Such terms as redox-half reaction pairs are used herein to include those members of the class of substance which provide the desired performance enhancement, rather than a mechanism of the chemistry occurring. Preferably, such compounds, when associated with the catalyst as salts of members of a half-reaction pair, are salts in which the anions are oxyanions, preferably an oxyanion of a polyvalent atom; that is, the atom of the anion to which oxygen is bonded is capable of existing, when bonded to a dissimilar atom, in different valence states. Potassium is the preferred cation and the preferred anions are nitrate, nitrite and other anions capable of undergoing displacement or other chemical reaction and forming nitrate anions under epoxidation or catalyst preparation conditions. Preferred salts include $KNO_3$ and $KNO_2$, with $KNO_3$ being most preferred.

Introduction Of Efficiency-Enhancing Salt To The Carrier

The efficiency-enhancing salt of a member of a redox-half reaction pair may be introduced to the catalyst in any known manner. Various sequences of impregnating or depositing silver and efficiency-enhancing salt on the surfaces of the carrier may be employed. Thus, impregnation and deposition of silver and an efficiency-enhancing salt of a member of a redox-half reaction pair may be effected coincidentally or sequentially, i.e., the salt or salts may be deposited prior to, during or subsequent to silver addition to the carrier. When more than one salt of a member of a redox-half reaction pair is employed, they may be deposited together or sequentially. It is preferred, however, to introduce the salts to the support in a single solution, rather than use sequential treatments using more than one solution and a drying step between impregnation steps, since the latter technique may result in leaching of the first introduced salt by the solution containing the second salt. Typical, and in many cases preferred, of such methods include concurrent, or coincidental, impregnation in which the solution which is used to impregnate the support with silver also contains at least one dissolved efficiency-enhancing salt member of a redox-half reaction pair. This procedure permits introduction of both the silver compound and the efficiency-enhancing salt simultaneously to the support in a single step and solution. The other commonly employed method is the sequential impregnation of the support in which initial introduction of the silver-containing solution or efficiency-enhancing salt solution (depending upon the sequence employed) is followed by drying of the silver-containing support (and heating and/or chemical reduction of the silver if this is the first added substance). This support is then impregnated with a solution of the second substance, that is, the efficiency-enhancing salt (if the silver was the first added substance). In order to perform the former procedure, i.e., coincidental impregnation, the efficiency-enhancing salt must be soluble in the same solvent or complexing/solubilizing liquid used with the silver-impregnating solution. With the sequential procedure in which the silver is added first, any solvent capable of dissolving the salt which will neither react with the silver nor leach it from the support is suitable. Aqueous solutions are generally preferred, but organic liquids, such as alcohols, may also be employed. Suitable procedures for effecting introduction of the efficiency-enhancing salt to the solid support may be found in many of the patents listed above.

In some instances, the coincidental method of preparation of the catalyst is decidedly less preferred or may not be used as, for example, where a barium, calcium or magnesium salt is intended to be solubilized and the solution contains materials which may precipitate the cation as, for instance, a carboxylic acid or dicarboxylic acid such as oxalic acid. p The salt of a member of a redox-half reaction pair is added in an amount sufficient to enhance the efficiency of the epoxidation reaction. The precise amount will vary depending upon such variables as the gaseous efficiency-enhancing member of a redox-half reaction pair of a redox-half reaction and concentration thereof employed, the concentration of other components in the gas phase, the amount of silver contained in the catalyst, the surface area of the support, the process conditions, e.g., space velocity and temperature, and morphology of support. Generally, however, a suitable range of concentration of the added efficiency-enhancing salt, calculated as cation, is about 0.01 to about 5 percent, preferably about 0.02 to about 3 percent, by weight, based on the total weight of the catalyst. Most preferably the salt is added in an amount of about 0.03 to about 2 weight percent.

It has been noted that when conventional analyses have been conducted with catalysts prepared by co-impregnation with silver and efficiency-enhancing salt, not all the anion associated with the cation has been accounted for. For example, catalysts prepared by co-impregnation with a potassium nitrate solution have been analyzed by conventional techniques and about 3 moles of the nitrate anion have been observed for every 4 moles of the potassium cation. This is believed to be due to limitations in the conventional analytical techniques and does not necessarily mean that the unaccounted for anions are not nitrate. For this reason, the amount of the efficiency-enhancing salt in the catalyst is given, in some instances, in terms of the weight percentage of the cation of the efficiency-enhancing salt (based on the weight of the entire catalyst), with the understanding that the anion associated with the cation is also present in the catalyst in an amount roughly proportional (on a molar basis) to the cation.

As indicated above, when the catalyst is intended to contain higher concentrations of silver, for example, equal to or above about 30 percent, by weight, it is generally preferred to use multiple cycles of impregnation and reduction to elemental silver. This seems to result in a more uniform distribution of silver throughout the catalyst pill. As with the catalyst containing lower amounts of silver introduced in a single impregnation, the introduction of the efficiency-enhancing salt of a member of a redox-half reaction pair may also be introduced in a sequential or coincidental procedure. Regardless of the method employed, a first cycle includes impregnation only with silver in an appropriate complexing/solubilizing agent followed by reduction to metallic silver, such as by roasting. (This is designated a "silver only" procedure.) If the sequential procedure is to be followed, the first cycle of impregnation and reduction is repeated one or more times. The final step includes impregnation with a solution of the efficiency-enhancing salt of a member of a redox-half reaction pair only, followed by draining and drying, as discussed above.

When preparing a catalyst containing a high concentration of silver and the coincidental or concurrent procedure is employed, the first cycle is the same as with the sequential procedure, i.e., an impregnation with silver and reduction (silver only). This is then followed either directly by a conventional coincidental impregnation (i.e., impregnation with a solution containing both silver in a soluble form and the efficiency-enhancing salt of a member of a redox-half reaction pair, followed by a reduction of silver to its elemental form, as by roasting) or by one or more repetitions of the impregnation cycle with a silver only procedure interposed between the first silver only cycle and the coincidental impregnation and reduction cycle. Suitable results have been obtained with both the sequential and coincidental procedures with two silver impregnation cycles, although there are indications that greater amounts of silver with more uniform distribution of silver throughout the pill can be obtained by three or possibly more silver-impregnation cycles. High silver-containing catalysts prepared by the coincidental impregnation technique provide somewhat better performance than those prepared by the sequential technique.

Epoxidation Procedure

As in conventional processes of this type, an alkene and an oxygen-containing gas are brought together in a reactor in the presence of a suitable epoxidation catalyst under epoxidation conditions. Typical epoxidation conditions include temperatures within the reaction zone of the reactor on the order of about 180 to 300 degrees C. and pressures from about 1 to about 30 atmospheres.

The gaseous efficiency-enhancing member of a redox-half reaction pair of a redox-half reaction pair may generally be supplied to the reaction zone within the reactor by introducing the component to the feedstream containing alkene and oxygen. Under commercial epoxidation conditions, such as those used in the present invention, the feedstream also contains a gas phase halogen compound, such as an alkyl halide, a hydrocarbon, and, when the effluent stream from the reactor is recycled, unreacted alkene. When recycle of the effluent stream is used, carbon dioxide may also be present. The presence and amount of carbon dioxide depends on, among other things, whether a scrubbing device is used.

The terms "gaseous member of a redox-half reaction pair", "gaseous efficiency-enhancing member of a redox-half reaction pair of a redox-half reaction pair", or like terms referred to herein have a meaning similar to that for the "salt of a member of a redox-half reaction pair" or like terms, defined above. That is, these terms refer to members of half-reactions, represented in standard or single electrode potential tables in standard reference texts or handbooks which are in a gaseous state and are substances which, in the reaction equations represented in the texts, are either oxidized or reduced. The preferred gaseous efficiency-enhancing materials are compounds containing an element capable of existing in more than two valence states, preferably nitrogen and another element which is, preferably, oxygen. Examples of preferred gaseous efficiency-enhancing member of a redox-half reaction pairs of redox-half reaction pairs include at least one of NO, $NO_2$, $N_2O_4$, $N_2O_3$ or any gaseous substance capable of forming one of the aforementioned gases, particularly NO and $NO_2$, under epoxidation conditions, and mixtures of one of the foregoing, particularly NO, with one or more of CO, $PH_3$, $SO_3$ and $SO_2$. NO is most preferred as the gaseous efficiency-enhancing member of a redox-half reaction pair.

Although in some cases it is preferred to employ members of the same half-reaction pair in the reaction system, i.e., both the efficiency-enhancing salt member associated with the catalyst and the gaseous member in the feedstream, as, for example, with a preferred combination of potassium nitrate and nitric oxide, this is not necessary in all cases to achieve satisfactory results. Other preferred combinations, such as $KNO_3/N_2O_3$, $KNO_3/NO_2$, $KNO_3/N_2O_4$, $KNO_2/NO$, $KNO_2/NO_2$, and $KNO_3$/a mixture of $SO_2$ and NO, may also be employed in the same system. In some instances, the salt and gaseous members may be found in different half-reactions which represent the first and last reactions in a series of half-reaction equations of an overall reaction.

The gaseous efficiency-enhancing member of a redox-half reaction pair of a redox-half reaction pair is also present in an amount sufficient to enhance the performance, such as the activity of the catalyst, and, particularly, the efficiency of the epoxidation reaction. The precise amount is determined, in part, by the particular efficiency-enhancing salt of a member of a redox-half reaction pair used and the concentration thereof, the particular alkene undergoing oxidation, and by other factors noted above which influence the amount of efficiency-enhancing salt of a member of a redox-half reaction pair. Typically a suitable concentration of the gaseous member of a redox-half reaction pair for epoxidation of most alkenes, including propylene, is about 0.1 to about 2,000 ppm, by volume, when $N_2$ is used as ballast. When a preferred gaseous member of a redox-half reaction pair, such as NO, is used in the epoxidation of propylene, the preferred concentration is about 5 to about 2,000 ppm, by volume, with an $N_2$ ballast. However, when ethylene is being oxidized, a suitable concentration is in the range of from about 0.1 to about 100 ppm, by volume, of the gaseous feedstream components. Preferably, when ethylene is being oxidized, the gaseous efficiency-enhancing member of a redox-half reaction pair is present in an amount of about 1 to about 80 ppm when about 3 percent, by volume, $CO_2$ is present. When nitric oxide is employed as the gaseous efficiency-enhancing member of a redox-half reaction pair in an ethylene epoxidation system, it is present in an amount of about 0.1 to about 60 ppm, preferably about 1 to about 40 ppm, when $CO_2$ is present.

The "oxygen-containing gas" employed in the reaction may be defined as including pure molecular oxygen, atomic oxygen, any transient radical species derived from atomic or molecular oxygen capable of existence under epoxidation conditions, mixtures of another gaseous substance with at least one of the foregoing, and substances capable of forming one of the foregoing under epoxidation conditions. Such oxygen-containing gas is typically introduced to the reactor either as air, commercially pure oxygen or other substance which under epoxidation conditions both exists in a gaseous state and forms molecular oxygen. The gaseous components which are supplied to the reaction zone, or that region of the reactor where reactants and catalyst are brought together under epoxidation conditions, are generally combined before being introduced to the reactor. The reactors in which the process and catalyst of the present invention are employed may be of any type known to the art. A brief description of several of the reactor parameters which may be used in the present invention are presented below.

In addition to an alkene, oxygen, and the gaseous efficiency-enhancing member of a redox-half reaction pair, the feedstream also contains a performance-enhancing halogen-containing compound, preferably an organic halide, including both saturated and unsaturated halides, such as ethylene dichloride, ethyl chloride, vinyl chloride, methyl chloride and methylene chloride. Preferably, in commercial production, ethylene chloride is employed as the halogen-containing compound. The amount of halide employed will vary depending upon a variety of factors, including the particular alkene being oxidized and the concentration thereof, the particular efficiency-enhancing salt and gaseous members of redox-half reaction pairs and the concentrations thereof, as well as other factors noted above as influencing the amount of efficiency-enhancing salt and gaseous compound. However, a suitable range of concentration for the halogen-containing compound in the oxidation of most alkenes, including propylene, is typically about 0.1 to about 2,000 ppm, by volume, of the gaseous makeup feedstream. When ethylene is oxidized, the range of concentration for the halogen-containing compound is, however, about 0.1 to about 60 ppm, by volume. In addition, a hydrocarbon, such as ethane, can be included in the feedstream. The feedstream may also contain a ballast or diluent, such as nitrogen, or other inert gas, particularly when air is used as the oxygen-containing gas. Varying amounts of carbon dioxide and water vapor may also be present, depending upon whether means have been provided to remove such substances from the effluent stream prior to combination of at least a portion of the effluent stream with the inlet stream. Other than the gaseous efficiency-enhancing member of a redox-half reaction pair of a redox-half reaction pair, the other components are typically present in amounts shown in the following tables for propylene and ethylene.

| Component | Volume Percent (or ppm) for Propylene Oxidation |
| --- | --- |
| propylene | about 2 to about 50 |
| oxygen | about 2 to about 10 |
| alkyl halide | about 5 to about 2,000 ppm |
| hydrocarbon | 0 to about 5 |
| carbon dioxide | up to about 15 |
| nitrogen or other ballast gas, e.g., methane | remainder. |

| Component | Volume Percent (or ppm) for Ethylene Oxidation |
| --- | --- |
| ethylene | at least about 2, often about 5 to about 50 |
| oxygen | about 2 to about 8 |
| alkyl halide | about 0.1 to about 60 ppm |
| hydrocarbon | 0 to about 5 |
| carbon dioxide | up to about 7 |
| nitrogen or other ballast gas, e.g., methane | remainder. |

When higher alkenes, such as those previously discussed, are epoxidized, conditions and concentrations typically used for the epoxidation of propylene may be employed.

Standard Alkene Oxide Process Test Conditions

The successful commercial production of alkene oxides, particularly ethylene oxide, by the silver-catalyzed oxidation of alkene, particularly ethylene, depends upon a variety of factors. Many of these factors influence, either directly or indirectly, the efficiency of the catalytic system, the activity or the aging rate of the catalyst. The manner in which catalysts and catalytic systems are evaluated in the laboratory strongly influences the values obtained for these parameters. Techniques and experiments designed to assess such catalysts and catalytic systems commonly employ microreactors (i.e., tiny tubular reactors for testing crushed catalyst particles) or back-mixed autoclaves of the Berty type (i.e., larger reactors which test full-sized catalyst pellets and generally employ full gas recycle) as described in FIG. 2 of the article by J. M. Berty, "Reactor For Vapor Phase-Catalytic Studies", *Chemical Engineering Progress*, 70, Number 5, pages 78–84 (1974), and particularly FIG. 2. Microreactors are capable of yielding, in most test situations, the highest efficiency numbers, typically approximately the same as or somewhat greater than those obtainable in commercial tubular reactor operations employing the same catalysts in non-crushed condition. Backmixed autoclaves commonly provide lower efficiency values because, although conditions can be varied, generally the entire catalyst is exposed to the outlet gas which has the lowest concentration of reactants and the highest concentration of products. Values obtained using one type of reactor are seldom identical to those obtained in another reactor system. As a result, claims of superior results or the desirability of one catalyst over another are preferably based on tests conducted under controlled and comparable conditions.

Although the conditions set forth supra may be employed both for reactors employed in commercial production as well as those employed in a laboratory, as a basis of comparison, the catalysts and catalytic systems for epoxidation of ethylene employed in the examples set forth below have been tested under comparable conditions known as Standard Alkene Oxide Process Test Conditions, or Standard Test Conditions (referred to hereinafter as STC). The STC employed for testing and characterizing the catalysts and the catalytic systems of the present invention involve the use of a standard back-mixed bottom-agitated "Magnedrive" autoclave or Berty autoclave, as described above.

In discussing the enhancement of efficiency provided by the present invention, it may be noted that, when an efficiency-enhancing amount of a salt of a member redox-half reaction pair is employed, an efficiency of at least about 84 percent is obtained under Standard Test Conditions. "Standard Test Conditions" for ethylene may be defined as comprising the following: by volume, 30 percent $C_2H_4$, 8 percent $O_2$, 5 ppm ethyl chloride, 5 ppm, by weight, NO, no added $C_2H_6$ or $CO_2$, $N_2$, ballast, 240 degrees C., 275 psig, gas hourly space velocity (GHSV)=8,000 $hr^{-1}$.

Although the present invention can be used with any size and type of alkene oxide reactor, including both fixed bed and fluidized bed reactors known to the art, it is contemplated that the present invention will find most widespread application in standard fixed bed, multi-tubular reactors. These generally include wall-cooled as well as adiabatic or non-wall-cooled reactors. Tube lengths may typically range from about 5 to about 60 feet but will frequently be in the range of from about 15 to about 40 feet. The tubes may have internal diameters from about 0.5 to about 2 inches and are expected to be typically from about 0.8 to about 1.5 inches. GHSV generally range from about 16,000 to about 1,000 $hr^{-1}$. Typically GHSV values range from about 2,000 to about 8,000 $hours^{-1}$ at pressures from about 1 to about 30 atmospheres, commonly about 10 to about 25 atmospheres.

While the invention is susceptible to various modifications and alternative forms, certain specific embodiments thereof are described in the examples set forth below. It should be understood, however, that these examples are not intended to limit the invention to the particular forms disclosed but, on the contrary, the invention is to cover all modifications, equivalents and alternatives falling within the spirit and scope of the invention.

EXAMPLE 1

Preparation Of A Fluorine-Containing Alpha-Alumina Support

Approximately 1,200 grams of ¼ inch hollow gamma-alumina pills or rings (obtained from Norton Corporation as Alumina 6573) were soaked for one-half hour in 1 molar $NH_4F$ with occasional shaking to liberate bubbles that formed during impregnation. Excess solution was drained from the rings, which were then dried overnight at 120 degrees C. The dried rings were distributed between four 3 inch diameter×6 inch deep cylindrical alumina crucibles and were fired in a P.D.H. high-temperature furnace. Lids for the crucibles were placed askew so that crucible openings were covered approximately 70 percent to maintain a fluoride atmosphere in the crucible but at the same time permit escape of excess fluoride. The firing schedule was one hour to raise the temperature to 700 degrees C., four hours to raise the temperature from 700 to 1,100 degrees C., and a hold temperature at 1,100 degrees C. for one hour. The product had a surface area of 1.56 $m^2/g$ and a sodium content of less than 50 ppm.

EXAMPLE 2

Sequential Preparation Of A Potassium Nitrate-Containing Supported Silver Catalyst Formation of a potassium nitrate-containing supported silver catalyst resulted from a multi-step procedure in which a support was initially impregnated with a silver-containing solution, the impregnated support was roasted, and the silver-impregnated catalyst was thereafter impregnated with a potassium nitrate solution and then dried.

The silver-containing solution used in the first step was prepared by dissolving 51.49 grams ethylenediamine in 51.03 grams of distilled water and stirring the mixture for a period of 10 minutes. To the stirred solution was slowly added 51.56 grams of oxalic acid dihydrate. The resulting solution was stirred for 10 minutes. To this solution was added, in portions, 90.34 grams silver oxide. The resulting silver-containing solution was thereafter stirred for an additional hour and 18.07 grams of monoethanolamine was then added to the stirred silver-containing solution. Stirring was continued for an additional 10 minutes. This solution was then diluted to a total volume of 437 ml by addition of distilled water.

In a catalyst-impregnation tube were placed 177.85 grams of an alpha-alumina carrier, similar to that prepared in Example 1. A catalyst-impregnation tube is an elongated tube, which in use is arranged vertically. The upper end of the tube is provided with an inlet to supply impregnation solution to the carrier contained in the tube and the lower end with an outlet from which solution may be drained. The tube is also provided with a means to connect the tube to a vacuum source. Prior to introduction of impregnation solution the tube was evacuated. The solution described immediately above was slowly poured into the tube to totally immerse the support. The carrier was allowed to remain in the impregnating solution for about 1 hour to achieve saturation of the support. The unabsorbed solution was thereafter drained from the support with draining continuing for about 30 minutes. The wet, impregnated carrier was then roasted in a hot-air belt roaster for 2.5 minutes at 500 degrees C. (66 SCFH air flow) to produce a catalyst containing 11.39 percent silver.

Upon cooling, 44.57 grams of the roasted, impregnated carrier was placed in an impregnation tube and covered with a solution formed by dissolving 2.08 grams potassium nitrate in 100 ml distilled water. After covering the roasted silver-containing carrier with the $KNO_3$-containing solution and allowing to stand for 15 minutes, the catalyst pellets were drained on a funnel for 5 minutes. The resulting drained pellets were dried in an oven for 2 hours at 120 degrees C., producing a catalyst containing 0.46 percent K, calculated as 1.20 percent $KNO_3$, by weight.

EXAMPLE 3

Preparation Of A Potassium Nitrate-Containing Silver Catalyst By A Co-Impregnation Technique A co-impregnation solution was prepared by placing 18.77 grams of ethylenediamine into a 400 ml beaker and mixing therewith 25 grams of distilled water to form a solution. To the stirred solution was slowly added 18.7 grams oxalic acid and, with continuous stirring, 35.2 grams of silver oxide was slowly added. When solution was complete, 6.55 grams of monoethanolamine were added directly to the solution. To the silver-containing solution were added 7.14 grams of a potassium nitrate solution, 10 percent with respect to potassium (0.258 grams KNO$_3$/g solution). To the resulting solution was added sufficient water to dilute the solution to 100 ml.

To make 100 ml of finished catalyst, 53.5 grams of an alpha-alumina support material of the type prepared in Example 1 but fired at a temperature of 1,000 degrees C. in the form of quarter-inch ring extrudate and having a pore volume of 0.62 g H$_2$O/g support were placed in an impregnation container. A source of vacuum was attached to the container and evacuated and thereafter the silver/potassium-containing impregnating solution was added, completely covering the carrier. After about one hour the excess solution was drained from the catalyst.

Roasting of the impregnated catalyst was conducted as indicated above in Example 2. The resulting catalyst included, by weight, 17 5 percent silver and, as calculated, about 1 percent potassium nitrate.

EXAMPLE 4

Sequential Preparation Of A Potassium Nitrate-Containing Supported High Silver Concentration Catalyst A solution containing 17.5 g ethylenediamine, 7.3 g distilled water, 17.5 g oxalic acid, 30.7 g silver oxide, 6.1 g monoethanolamine, diluted to 125 ml, was prepared in the manner described in Example 2.

Into a catalyst impregnation tube were placed 43.9 g of an alpha-alumina carrier, similar to that prepared in Example 1, and having a surface area of 1.12 m$^2$/g, a pore volume of 0.8 cc/g, less than 50 ppm, by weight, leachable sodium, and a platelet morphology. The support pellets were initially vacuum-impregnated at 28 inches mercury vacuum, releasing the vacuum when the pellets were completely covered with the aqueous silver amine solution, permitting them to stand in the amine solution for an additional hour at 1 atmosphere before draining. The impregnated pellets were then belt-roasted at 500 degrees C. in an oven having an air flow of 66 SCFH for 2.5 minutes. The material contained 14.9 percent silver as determined by weight gain. This material was then impregnated a second and third time with fresh silver/amine solution having the composition indicated above. The impregnations and belt-roastings were conducted in the same manner as described above. The catalyst material was then impregnated with KNO$_3$ by placing 67.4 g of the silver-impregnated pellets into a solution containing 2.1 g KNO$_3$ dissolved in 100 ml distilled water. The KNO$_3$-impregnated silver catalyst material was then dried at 120 degrees C. for 1 hour to yield a catalyst containing, by weight, 34.7 percent silver and 0.33 percent K (calculated as 0.86 percent KNO$_3$), as determined by weight gain.

EXAMPLE 5

Coincidental Preparation Of A Potassium Nitrate-Containing Supported High Silver Concentration Catalyst A silver impregnation solution was prepared in a manner similar to that described in Example 2 by mixing 196.8 g ethylenediamine, 195.0 g distilled water, 197.1 g oxalic acid, 345.2 g silver oxide, 69.1 g monoethanolamine and diluting to a total volume of 780 ml with distilled water. After evacuation of an impregnation tube containing pellets of an alpha-alumina support material (293.1 g) similar to those described in Example 1 and having a B.E.T. surface area of 1.16 m$^2$/g as measured by a QUANTASORB TM apparatus, the pellets were impregnated by allowing them to stand in the silver impregnation solution for a period of 1 hour and then draining. The impregnated pellets were then belt-roasted at 500 degrees C. in a 66 SCFH air flow for 2.5 minutes. As determined by gain in weight, the material contained 24.6 percent silver.

A co-impregnation solution was prepared in a manner similar to that described in Example 3 by mixing 37.5 g ethylenediamine, 37.2 g distilled water, 37.6 g oxalic acid, 65.9 g silver oxide, 13.2 g monoethanolamine, and 0.80 g potassium nitrate and diluting to 150 ml total solution with distilled water. The silver-impregnated catalyst pellets (77.8 g) were impregnated by immersing them in the silver/potassium nitrate-impregnating solution for 1 hour and then draining. The resulting pellets were then belt-roasted as described above. The pellets resulting from the two impregnations yielded a material, as determined by an analysis, containing, by weight, 39.8 percent silver and 0.098 percent K (calculated as 0.25 percent KNO$_3$).

EXAMPLES 6 to 11

Production Of Ethylene Oxide With Potassium Nitrate-Containing Supported Silver Catalyst The examples set forth below were conducted employing catalyts using carriers of the type prepared in Example 1, the catalysts themselves being prepared in the manner described in Examples 2 and 3 and identified as being prepared by either a sequential (S) procedure or a coincidental impregnation (C) procedure. The epoxidation studies for which data are presented below were conducted in a continuously stirred tank reactor, also known as a back-mixed autoclave of the type described above. The procedure involved charging approximately 80 ml of catalyst to the autoclave. The volume of catalyst was measured in a one inch I.D. graduated cylinder after tapping the cylinder several times to thoroughly pack the catalyst. The weight of the catalyst was noted and is indicated in the table appearing below. The backmixed autoclave was heated to about reaction temperature in a nitrogen flow of 11.3 SCFH with the fan operating at about 1,500 rpm. The nitrogen flow was then discontinued and the feedstream was introduced to the reactor.

All ethylene epoxidation reactions, except where indicated otherwise, were examined under Standard Test Conditions comprising, by volume, 30 percent C$_2$H$_4$, 8 percent O$_2$, 5 ppm ethyl chloride, 5 ppm, by weight, NO, no added C$_2$H$_6$ or CO$_2$, N$_2$ ballast, 240 degrees C., 275 psig, GHSV=8,000 hr$^{-1}$. The data summarized below includes surface areas of the catalysts, Ag and calculated KNO$_3$ contents, maximum observed outlet ethylene oxide (activity), maximum observed efficiency, and aging rate.

TABLE

| Example | Preparation Procedure | S.A. (m$^2$/g) | % Ag | % KNO$_3$ | Maximum Activity (E.O.) | Maximum Efficiency |
|---|---|---|---|---|---|---|
| 6 | C | 0.7 | 19.7 | 2.0 | 1.18 | 91.00 |
| 7 | C | 1.4 | 20.0 | 2.0 | 1.41 | 90.25 |
| 8 | C | 1.1 | 19.7 | 2.0 | 1.23 | 90.00 |

TABLE-continued

| Example | Preparation Procedure | S.A. (m²/g) | % Ag | % KNO₃ | Maximum Activity (E.O.) | Maximum Efficiency |
|---|---|---|---|---|---|---|
| 9 | C | 0.8 | 20.4 | 2.0 | 1.35 | 90.25 |
| 10 | S | 1.0 | 15.6 | 1.0 | 1.12 | 86.5 |
| 11 | S | 1.0 | 15.6 | 2.0 | 1.18 | 88.5. |

EXAMPLE 12

Production of Propylene Oxide With Potassium Nitrate-Containing Supported Silver Catalyst Into a back-mixed autoclave, having a slightly smaller volume than the autoclave employed in the previous examples, were placed 5.0 grams (10.0 ml) of a catalyst having a support prepared as in Example 1. The support was an alpha-alumina having a surface area of 1.12 m²/g, a pore volume of 0.8 cc/g, less than 50 ppm, by weight, of leachable sodium, a residual fluorine concentration of 0.7 percent, and a platelet morphology. The catalyst included, by weight, a silver concentration of 17.7 percent and a potassium concentration of 0.38 percent (calculated as 1 percent potassium nitrate). A mixture, by volume, of 9.9 percent propylene, 7.75 percent oxygen, 200 ppm ethyl chloride, 200 ppm nitric oxide, 2 percent methane, and the remainder being nitrogen ballast gas, was fed to the reactor at a temperature of 252 degrees C., a pressure of 25 psi and a gas hourly space velocity of 832 hr⁻¹. After 22.5 hours, a selectivity of 47.3 percent was observed with an activity of 0.6 pounds of propylene oxide/cubic foot of catalyst/hour (corresponding to an outlet percent of propylene oxide of 0.465 percent).

I claim:

1. A process for the epoxidation of alkene in the presence of an oxygen-containing gas comprising said alkene and the oxygen-containing gas under epoxidation conditions in the presence of at least one gaseous member of a redox-half reaction pair comprising NO, $NO_2$, $N_2O_3$, $N_2O_4$, or a gas capable of generating one of the above-mentioned gases under epoxidation conditions and a supported silver catalyst, said catalyst comprising a catalytically effective amount of silver on a solid, porous support having an efficiency-enhancing amount of at least one efficiency-enhancing nitrate salt, said support consisting essentially of alpha-alumina and having a surface area of at least about 0.7 m²/g and at least 50 percent of the support particles having particle sizes of at least 0.1 micron have a platelet-type morphology.

2. The process of claim 1 wherein said gas capable of generating one of the aformentioned gases generates at least one of NO and $NO_2$.

3. The process of claim 1 wherein said at least one efficiency-enhancing salt of a member of a redox-half reaction pair comprises potassium nitrate.

4. The process of claim 1 wherein said at least one gaseous member comprises nitrogen monoxide or nitrogen oxide and said at least one salt comprises potassium nitrate.

5. The process of claim 1 wherein the support has a surface area of about 0.7 to about 7 m²/g.

6. The process of claim 1 wherein the median pore diameter is about 1 to about 5 microns.

7. The process of claim 1 wherein the major dimension of substantially all the particles having platelet-type morphology is less than about 50 microns.

8. The process of claim 7 wherein the major dimension of substantially all the particles having platelet morphology is less than about 20 microns.

9. The process of claim 1 wherein said alkene comprises ethylene.

10. The process of claim 1 wherein said alkene comprises propylene.

* * * * *

UNITED STATES PATENT AND TRADEMARK OFFICE
CERTIFICATE OF CORRECTION

PATENT NO. : 4,994,589

DATED : February 19, 1991

INVENTOR(S) : T.M. Notermann

It is certified that error appears in the above-identified patent and that said Letters Patent is hereby corrected as shown below:

Column 14, line 62, after "1" insert --hour. However, with lower concentrations of fluorine--.

Signed and Sealed this

Twenty-seventh Day of October, 1992

Attest:

DOUGLAS B. COMER

Attesting Officer        Acting Commissioner of Patents and Trademarks